US000001345H

United States Statutory Invention Registration [19]

[11] Reg. Number: H1345

[43] Published: Aug. 2, 1994

Biller

[54] METHOD FOR PREVENTING OR TREATING HEPATITIS D

[75] Inventor: Scott A. Biller, Ewing, N.J.

[73] Assignee: Bristol-Myers Squibb Company, Princeton, N.J.

[21] Appl. No.: 968,079

[22] Filed: Oct. 28, 1992

[51] Int. Cl.[5] ..... A61K 31/66
[52] U.S. Cl. ..... 514/108
[58] Field of Search ..... 514/108

[56] References Cited

U.S. PATENT DOCUMENTS 4,871,721 10/1989 Biller ..... 514/102
5,025,003 6/1991 Biller ..... 514/120
5,157,027 10/1992 Biller et al. ..... 514/107

OTHER PUBLICATIONS

Glenn, Jeffrey S. et al, "Identification of a Prenylation Site in Delta Virus Large Antigen", Science, vol. 256, pp. 1331–1333, May 29, 1992.

*Primary Examiner*—Robert L. Stoll
*Assistant Examiner*—Joseph D. Anthony
*Attorney, Agent, or Firm*—Burton Rodney

[57] ABSTRACT

A method is provided for blocking or preventing the prenylation of CXXX box containing proteins thereby preventing and/or treating hepatitis D which includes the step of administering a therapeutically effective amount of a protein-prenyl transferase inhibitor.

7 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR PREVENTING OR TREATING HEPATITIS D

FIELD OF THE INVENTION

The present invention relates to a method for treating and/or preventing hepatitis delta virus (also referred to as hepatitis D) by blocking the prenylation of CXXX box containing proteins by administering a therapeutic amount of a protein-prenyl transferase inhibitor.

BACKGROUND OF THE INVENTION

J. Glenn et al, "Identification of a Prenylation Site in Delta Virus Large Antigen", Science, Vol. 256, 29 May 1992, pp. 1331–1333, discloses that during replication, hepatitis delta virus (HDV) switches from production of small to large delta antigen which is prenylated and packaged into virus particles.

The last four amino acids of large delta antigen are Cys-Arg-Pro-Gln-COOH. This COOH-terminal configuration is termed a CXXX box, where C is cysteine and X is any amino acid.

The CXXX box has been implicated as a substrate for prenyltransferases that add to the cysteine 15 (farnesyl) or 20 (geranylgeranyl) carbon moieties derived from mevalonic acid. (J. A. Glomset et al, Trends Biochem. Sci. 15, 139 (1990); W. A. Maltese, FASEB J. 4, 3319 (1990); S. L. Moores et al, J. Biol. Chem. 266, 14603 (1991)).

Glenn et al determined that large delta antigen undergoes prenylation in cultured cells and thus is a substrate for prenylation which is required for productive viral infection. In fact, Glenn et al found that mutation of $Cys^{211}$ (the only cysteine in large delta antigen) in the CXXX box of the large delta antigen abolished both prenylation and viral particle formation. In conclusion, Glenn et al suggest "prenylation as a new target for anti-HDV therapy." As strategies designed to interfere with the prenylation stage of the HDV life cycle, Glenn et al suggest "drugs that inhibit enzymes along the prenylation pathway, and CXXX box analogs." (See page 1332).

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds," Vol. I, Chapter 8, pp. 413–441, J. Wiley and Sons, 1981, and references therein). This enzyme is the first committed step of the de novo cholesterol biosynthetic pathway.

Squalene synthetase inhibitors which block the action of squalene synthetase (after the formation of farnesyl pyrophosphate) are disclosed in U.S. Pat. Nos. 4,871,721 and 5,025,003, U.S. application Ser. No. 501,204, filed Mar. 29, 1990, and U.S. application Ser. No. 699,429, filed May 13, 1991.

DESCRIPTION OF THE INVENTION

In accordance with the present invention, it has been found that post-translational modification of CXXX box containing proteins may be inhibited by administering a protein-prenyl transferase inhibitor which inhibits the transfer of the prenyl group (such as farnesyl, geranyl or geranylgeranyl) to the cysteine of the CXXX box by the protein-prenyl transferase enzyme. The protein-prenyl transferase inhibitor will block the protein-prenyl transferase enzyme from catalyzing the transfer of the prenyl group (for example, farnesyl, geranyl or geranylgeranyl) from the prenyl pyrophosphate to the cys residue of the CXXX box. Prenylation being prevented, productive HDV viral infection (hepatitis delta virus) is inhibited.

Thus, the present invention resides in a method for blocking or preventing the prenylation of CXXX box containing proteins such as large delta antigen, and thereby inhibit disease promoting effects of the CXXX box containing protein or more specifically prevent and/or treat hepatitis D viral infection, by administering to a patient in need of treatment a therapeutic amount of a protein-prenyl transferase inhibitor.

The protein-prenyl transferase inhibitors, unlike HMG CoA reductase inhibitors, will interfere with prenylation of the large delta antigen and inhibit their transforming activity, yet may or may not interfere with the synthesis of FPP, a precursor in the synthesis of ubiquinones, dolichols and Haem A.

The activity of the protein-prenyl transferase inhibitors in blocking the protein-prenyl (e.g. farnesyl, geranyl or geranylgeranyl) transferase from catalyzing the transfer of the prenyl group (e.g. farnesyl, geranyl or geranylgeranyl) from the prenyl pyrophosphate to the cys residue of the CXXX box may be assayed by a procedure similar to that described in U.S. application Ser. No. 520,570 filed May 8, 1990, by Barbacid et al, the disclosure of which is incorporated herein by reference.

Protein-prenyl transferase inhibitors suitable for use herein include compounds disclosed in U.S. application Serial No. 699,429 filed May 13, 1991, by Biller et al. These protein-prenyl transferase inhibitors have the following structure

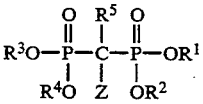

I wherein $R^1$, $R^2$, $R^3$ and $R^4$ are the same or different and are H, alkyl, a metal ion or a prodrug ester;

$R^5$ is H, halogen or lower alkyl;

Z a lipophilic group containing at least 6 carbons and can be substituted alkenyl wherein the alkenyl group contains from 7 to 25 carbon atoms in the chain and from 1 to 4 double bonds; substituted alkynyl containing 1 to 4 triple bonds; mixed alkenyl-alkynyl containing 1 to 3 double bonds and 1 to 3 triple bonds and wherein alkenyl and/or alkynyl may be substituted or unsubstituted; or a substituted phenylalkyl group of the structure

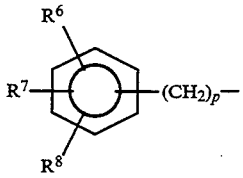

wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, preferably from 3 to 15 carbons, alkoxy containing 1 to 40 carbons, preferably from 3 to 15 carbons, alkenyl containing 2 to 40 carbons, preferably from 3 to 15 carbons, alkenyloxy containing 2 to 40 carbons, preferably from 3 to 15 carbons, alkynyl containing 2 to 40 carbons, preferably from 3 to 15 carbons, alkynyloxy containing 2 to 40 carbons, preferably from 3 to 15 carbons, aryloxy, hydroxy, halogen, nitro, amino, thiol, alkylthio, arylthio, alkylsulfinyl, arylsulfinyl, alkylsulfonyl, arylsulfonyl, carboxy, alkoxycarbonyl, aminocarbonyl, alkylcarbonyloxy, arylcarbonyloxy, arylcarbonylamino or alkylcarbonylamino, at least one of $R^6$, $R^7$ and $R^8$ being alkenyl, alkenyloxy, alkynyl or alkynyloxy; and wherein the total number of carbons in the substituted phenylalkyl group exceeds 10 carbons.

The terms "substituted alkenyl" and "substituted alkynyl" as employed herein with respect to Z refers to alkenyl or alkynyl substituted with 1 to 4 groups which may be alkyl, alkenyl, alkynyl, halogen, hydroxy, alkoxy, alkenyloxy, alkynyloxy, aryl and/or cycloalkyl.

The $(CH_2)_p$ group may contain one or more alkyl, alkoxy, alkenyl, alkynyl, hydroxy and/or halogen substituents.

Preferred embodiments of formula I protein-prenyl transferase inhibitors have the structure

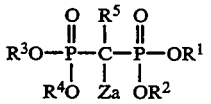

II wherein $R^1$, $R^2$, $R^3$, $R^4$ and $R^5$ are as defined above and Za is substituted alkenyl which includes from 1 to 4 double bonds and is substituted with from 1 to 4 alkyl groups.

In addition, other protein-prenyl transferase inhibitors suitable for use herein and disclosed in application Ser. No. 699,429 have the structure

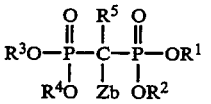

III wherein Zb is

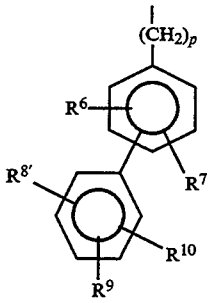

wherein $R^1$, $R^2$, $R^3$, $R^4$, $R^5$, $R^6$, $R^7$ and $(CH_2)_p$ are as defined hereinbefore, except that $R^6$ and $R^7$ may be any one of the groups included under the definition $R^6$ and $R^7$, set out hereinbefore, without limitation; $R^{8'}$, $R^9$ and $R^{10}$ are the same or different and are as defined hereinbefore with respect to $R^6$ and $R^7$, without limitation.

Preferred are compounds of formula III wherein the $R^{8'}$, $R^9$phenyl is para to the $R^6$, $R^7$-phenylene. These compounds have been found to inhibit cholesterol biosynthesis when administered orally.

In another embodiment of the present invention, compounds which are protein-prenyl transferase inhibitors (disclosed in Ser. No. 699,429) may be employed which have the structure

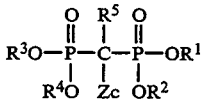

IV wherein $R^1$, $R^2$, $R^3$, $R^4$ and R5 are as defined hereinbefore and Zc is alkyl wherein the alkyl group contains from 9 to 14 carbons in the normal chain and is substituted with 1, 2, 3 or 4 alkyl groups.

Still another embodiment of compounds which are protein-prenyl transferase inhibitors (disclosed in Ser. No. 699,429) have the structure

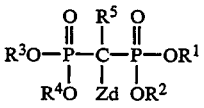

V wherein Zd is

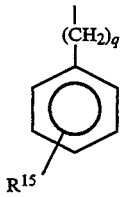

wherein $R^1$, $R^2$, $R^3$, $R^4$ and R5 are as defined hereinbefore and $(CH_2)_q$ contains at least 2 carbons in the chain and may include 0, 1, 2 or 3 double bonds and/or 0, 1, 2 or 3 triple bonds in the normal chain, preferably 3 to 7 carbons in the normal chain, and may include one or more alkyl, alkenyl, alkynyl, alkoxy, hydroxy and/or halogen substituents; and $R^{15}$ is alkyl containing from 2 to 20 carbons, and preferably is in the para position, and the total number of carbons in Zd exceeds 10.

Other protein-prenyl transferase inhibitors suitable for use herein are compounds disclosed in U.S. application Ser. No. 501,204 filed Mar. 29, 1990, by Biller et al and have the following structure

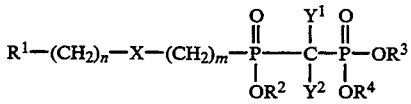

VI wherein m is 0, 1, 2 or 3; n is 0, 1, 2, 3 or 4; $Y^1$ and $Y^2$ are H or halogen, preferably H or F; $R^2$, $R^3$ and $R^4$ are independently H, metal ion. $C_1$ to $C_8$ alkyl or $C_3$ to $C_{12}$ alkenyl; X is O, NH,

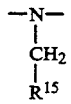

or S (wherein $R^{15}$ is H or $C_1$ to $C_5$ alkyl); $R^1$ is $R^5$—Q-$^1$—$Q^2$-13 $Q^3$—wherein $Q^1$, and $Q^2$ and $Q^3$ are independently:

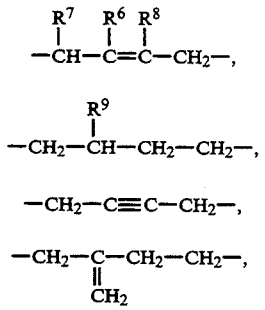

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, halo or haloalkyl (e.g. $CH_2F$, $CF_3$); $R^7$ is H, halogen, lower alkyl or alkylthio; $R^8$ is H, halogen, trimethylsilyl or lower alkyl; $R^9$ is H, or lower alkyl; $R^5$ is

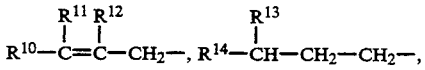

$R^{16}$—C≡C—$CH_2$—(wherein $R^{16}$ is lower alkyl or H),

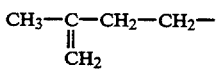

or $CH_3(CH_2)_p$—where p is 2 to 7; $R^{10}$ and $R^{11}$ are independently hydrogen, lower alkyl such as methyl or ethyl, halogen, lower alkenyl or haloalkyl $R^{10}$ or and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl; with the provisos that if all of $Q^1$, $Q^2$ and $Q^3$ are bonds, then $R^{10}$ and $R^{11}$ cannot both be H, and $R^5$ cannot be $CH_3(CH_2)_p$—, with $p \leqq 4$; if m is o, X is other than S; and if m is o and X is O, then n is 1, 2, 3 or 4, including all stereoisomers thereof.

The term "lower alkenyl" or "alkenyl" as used above by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

Preferred are those compounds of formula VI which have the following formula: VII

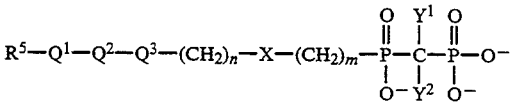

wherein $R^5$ is

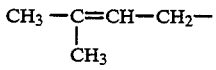

$Q^3$ is a bond;
$Q^2$ is

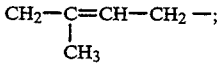

—$CH_2$—C≡C—$CH_2$—: or —$CH_2$—CH=CH—$CH_2$—;
$Q^1$ is

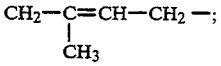

n is 0 or 1; m is 1 or 2; X is O and $Y^1$ and $Y^2$ are each H or F, in the form of the salts or acid.

In addition, preferred are those compounds of formula VI which have the following structure VIA-A

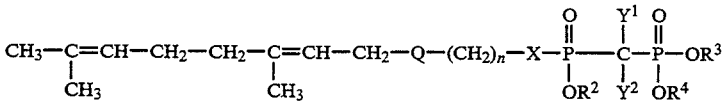

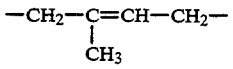

wherein Q is or a bond; n is 1 or 2; X is O, $Y^1$ and $Y^2$ are each H or each F; $R^2$, $R^3$ and $R^4$ are alkyl, H or metal ions; or X is NH and n is 0.

In addition, protein-prenyl transferase inhibitors which may be employed herein include compounds disclosed in U.S. Pat. No. 5,025,003 to Biller and have the following structure

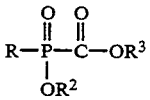

VIII wherein $R^2$ is a metal ion, lower alkyl or H;

$R^3$ is a metal ion or lower alkyl;

R is $R^1$—$(CH_2)_n$—, $R^1$—$(CH_2)_m$O—or $R^1$—$(CH_2)_m$$OCH_2$—, wherein n is 1 to 4, m is 0 to 3; and $R^1$ is $R^5$—$Q^1$—$Q^2$—$Q^3$—wherein $Q^1$, $Q^2$ and $Q^3$ are independently:

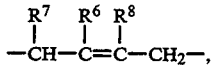

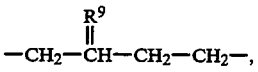

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, fluoro or fluoroalkyl (e.g., $CH_2F$, $CF_3$); $R^7$ is H, fluoro, lower alkyl or alkylthio; $R^8$ is H, fluoro, trimethylsilyl or lower alkyl; $R^9$ is H, or lower alkyl; $R^5$ is

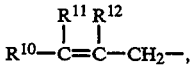

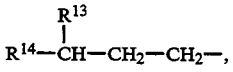

(wherein $R^{16}$ is lower alkyl or H), or $CH_3(CH_2)_p$— where p is 2 to 7; $R^{10}$ and $R^{11}$ are independently hydrogen, lower alkyl such as methyl or ethyl, fluoro, lower alkenyl or fluoroalkyl or $R^{10}$ and $R^{11}$ can be taken together to form $(CH_2)_s$, where s is 2 7; $R^{12}$ is hydrogen, lower alkyl, fluoro or lower alkenyl; $R^{13}$ and $R^{14}$ are independently lower alkyl such as methyl or ethyl; with the proviso that if all of $Q^1$, $Q^2$ and $Q^3$ are bonds, then $R^{10}$ and $R^{11}$ cannot both be H, and $R^5$ cannot be $CH_3(CH_2)_p$, with $p<4$, including all stereoisomers thereof.

The term "lower alkenyl" or "alkenyl" as used herein is defined hereinbefore.

Preferred are those compounds of formula VIII wherein $R^1$ is

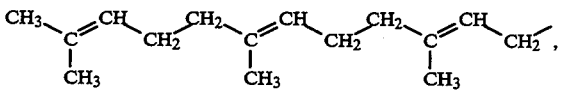

n is 1, 2 or 3, m is 1 or 2, $R^2$ is H or a metal ion, and $R^3$ is lower alkyl, a metal ion or H.

Other protein-prenyl transferase inhibitors suitable for use herein include compounds disclosed in U.S. Pat. No. 4,871,721 to Biller and have the following structure:

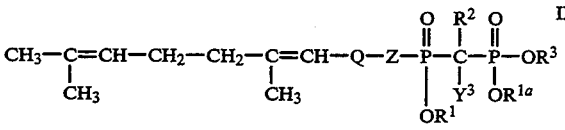

IX wherein

Q is

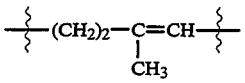

Z is —$(CH_2)$hd n—or —$(CH_2)_p$—CH=CH—$(CH_2)_m$, wherein n is 1 to 5; p is 0, 1 or 2; m is 0, 1 or 2;

R, $R^1$ and $R^{1a}$ may be the same or different and are H, lower alkyl or a metal ion; and $R^2$ and $R^3$ may be the same or different and are H or halogen.

Preferred are those compounds of formula IX which have the following structure

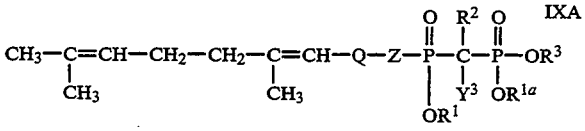

IXA wherein

Q is

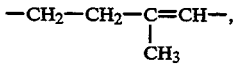

Z is —$CH_2CH_2$—or —CH=CH—; $R^2$ and $R^3$ are each H or each F; R, $R^1$ and $R^{1a}$ are OH or metal ions.

Other protein-prenyl transferase inhibitors suitable for use herein (disclosed in U.S. application Ser. No. 950,555, filed Sep. 25, 1992) has the structure

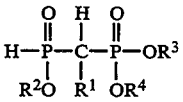

wherein $R^2$, $R^3$ and $R^4$, are independently H, alkyl, a metal ion or a prodrug ester; and $R^1$ is a lipOphilic group containing at least 6 carbons, and including pharmaceutically acceptable salts thereof.

$R^1$ is alkyl, alkenyl, alkynyl or aryl.

More specifically $R^1$ is alkenyl containing from 7 to 25 carbon atoms in the chain and from 1 to 4 double bonds; alkynyl containing 1 to 4 triple bonds; mixed alkenyl-alkynyl containing 1 to 3 double bonds and 1 to 3 triple bonds, and where in the above groups alkyl, alkenyl and/or alkynyl may be substituted or unsubstituted; or a group of the structure

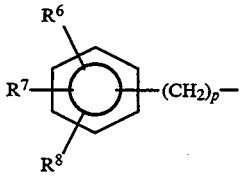

wherein $(CH_2)_p$ contains from 1 to 15 carbons in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, aryl, aryloxy, hydroxy, halogen, nitro, amino, thiol, alkylthio, arylthio, alkylsulfinyl, arylsulfinyl, alkyl-sulfonyl, arylsulfonyl, carboxy, alkoxycarbonyl, aminocarbonyl, alkylcarbonyloxy, arylcarbonyloxy, arylcarbonylamino or alkylcarbonylamino.

The disclosures of the above U.S. patents and U.S. patent applications are incorporated herein by reference. The preferred compounds in these patents and patent applications are the preferred compounds for use in the method of the invention.

In carrying out the method of the invention, a pharmaceutical composition will be employed containing at least one protein-prenyl transferase inhibitor in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains protein-prenyl transferase inhibitor (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of sterile protein-prenyl transferase inhibitor into a vial, aseptically freeze-drying and sealing. For use, the contents of the vial are mixed with 2 mL of physiological saline, to produce an injectable preparation.

What is claimed is:

1. A method for treating and/or preventing hepatitis D, which comprises administering to a mammalian species in need of treatment a therapeutically effective amount of a protein-prenyl transferase inhibitor.

2. The method as defined in claim 1, wherein the protein-prenyl transferase inhibitor has the structure

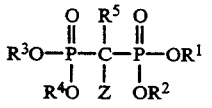

wherein $R^1$, $R^2$, $R^3$ and $R^4$ are the same or different and are H, lower alkyl, a metal ion or a prodrug ester;

$R^5$ is H, halogen or lower alkyl;

Z is substituted alkenyl wherein the alkenyl group contains at least 7 carbon atoms in the chain and from 1 to 4 double bonds; substituted alkynyl containing 1 to 4 triple bonds; mixed alkenyl-alkynyl containing 1 to 3 double bonds and 1 to 3 triple bonds, and wherein alkenyl and/or alkynyl may be substituted or unsubstituted; or a substituted phenylalkyl group of the structure

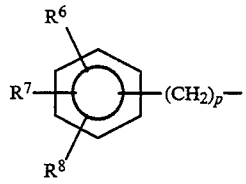

wherein $(CH_2)_p$ contains from 1 to 15 carbons in the chain and may include 0, 1, 2 or 3 double bonds and/or 0, 1, 2 or 3 triple bonds in the normal chain and/or may include 0, 1, 2 or 3 substituents which are alkyl, alkenyl, alkoxy, alkynyl, hydroxy and/or halogen; and $R^6$, $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino alkylcarbonylamino, at least one of $R^6$, $R^7$ and $R^8$ being alkenyl, alkenyloxy, alkynyl or alkynyloxy, and wherein the total number of carbons in

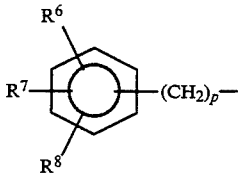

exceeds 10 carbons.

3. The method as defined in claim 1, wherein the protein-prenyl transferase inhibitor is a bisphosphonate.

4. The method as defined in claim 3, wherein the protein-prenyl transferase inhibitor has the structure

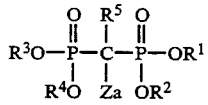

wherein $R^1$, $R^2$, $R^3$ and $R^4$ are the same or different and are H, alkyl, a metal ion or a prodrug ester; $R^5$ is H, halogen or alkyl, and Za is substituted alkenyl which includes 1 to 4 double bonds and is substituted with from 1 to 4 lower alkyl groups.

5. The method as defined claim 3, wherein the protein-prenyl transferase inhibitor has the structure

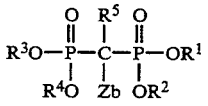

wherein

Zb is

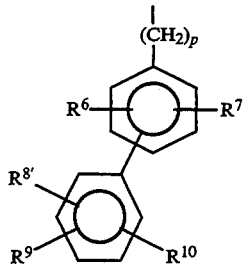

$R^1$, $R^2$, $R^3$ and $R^4$ are the same or different and are H, alkyl, a metal ion or a prodrug ester;

$R^5$ is H, halogen or alkyl;

p is 1 to 15;

$(CH_2)_p$ may include 0, 1, 2 or 3 double bonds and/or 0, 1, 2 or 3 triple bonds in the normal chain, and/or may include 0, 1, 2 or 3 substituents which are alkyl, alkoxy, alkenyl, alkynyl, hydroxy and/or halogen and $R^6$, $R^7$, $R^{8'}$, $R^9$ and $R^{10}$ are the same or different and are H, alkyl containing 1 to 40 carbons, alkoxy containing 1 to 40 carbons, alkenyl containing 2 to 40 carbons, alkenyloxy containing 2 to 40 carbons, hydroxy, alkynyl containing 2 to 40 carbons, alkynyloxy containing 2 to 40 carbons, aryloxy, halogen, nitro, amino, thio, alkylthio, arylthio, arylsulfinyl, alkylsulfinyl, arylsulfonyl, alkylsulfonyl, carboxy, alkycarbonyloxy, arylcarbonyloxy, alkoxycarbonyl, aminocarbonyl, arylcarbonylamino or alkylcarbonylamino.

6. The method as defined in claim 3, wherein the protein-prenyl transferase inhibitor has the structure

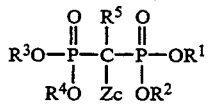

wherein

Zc is substituted alkyl containing from 9 to 14 carbons in the normal chain and is substituted with 1 to 4 lower alkyl groups;

$R^1$, $R^2$, $R^3$ and $R^4$ are the same or different and are H, alkyl, a metal ion or a prodrug ester; and $R^5$ is H, halogen or alkyl.

7. The method as defined in claim 3, wherein the protein-prenyl transferase inhibitor has the structure

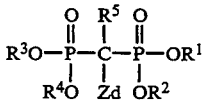

wherein

Zd is

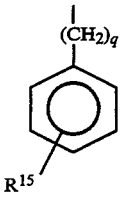

q is 2 to 15, $(CH_2)_q$ may include 0, 1, 2 or 3 double bonds and/or 0, 1, 2 or 3 triple bonds in the normal chain and may optionally include one or more alkyl, alkenyl, alkynyl, hydroxy, alkoxy and/or halogen substituents;

$R^1$, $R^2$, $R^3$ and $R^4$ are the same or different and are H, alkyl, a metal ion or a prodrug ester; and $R^5$ is H, halogen or lower alkyl; and $R^{15}$ is alkyl containing from 2 to 20 carbons;

the total number of carbons in Zd exceeds 10.

* * * * *